(12) United States Patent
Iyer et al.

(10) Patent No.: US 8,478,409 B2
(45) Date of Patent: Jul. 2, 2013

(54) FILTERING CAPACITOR FEEDTHROUGH ASSEMBLY

(75) Inventors: Rajesh V. Iyer, Eden Prairie, MN (US); Richard P. Millis, Blaine, MN (US); Michael G. Marinkov, Woodbury, MN (US); Micah A. Litow, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 222 days.

(21) Appl. No.: 13/072,204

(22) Filed: Mar. 25, 2011

(65) Prior Publication Data

US 2011/0170230 A1    Jul. 14, 2011

Related U.S. Application Data

(62) Division of application No. 11/688,985, filed on Mar. 21, 2007, now Pat. No. 7,917,218.

(51) Int. Cl.
*A61N 1/06* (2006.01)
(52) U.S. Cl.
USPC ............. 607/36; 607/37; 607/38; 439/909
(58) Field of Classification Search
USPC ............ 607/36–38; 439/909; 174/650, 659, 174/664, 50, 52; 333/182; 361/307
See application file for complete search history.

(56) References Cited

U.S. PATENT DOCUMENTS

| | | | |
|---|---|---|---|
| 1,488,175 A | 3/1924 | Strandell | |
| 3,343,122 A | 9/1967 | Drogo | |
| 3,449,708 A | 6/1969 | Roland et al. | |
| 4,784,141 A | 11/1988 | Peers-Trevarton | |
| 4,934,366 A | 6/1990 | Truex et al. | |
| 4,966,564 A | 10/1990 | Foote | |
| 4,997,380 A | 3/1991 | Etienne et al. | |
| 5,012,807 A | 5/1991 | Stutz, Jr. | |
| 5,251,986 A | 10/1993 | Arena | |
| 5,333,095 A | 7/1994 | Stevenson | |
| 5,573,000 A | 11/1996 | Goffer et al. | |
| 5,905,627 A | 5/1999 | Brendel | |
| 6,275,369 B1 | 8/2001 | Stevenson | |
| 6,660,116 B2 | 12/2003 | Wolf | |
| 6,765,779 B2 | 7/2004 | Stevenson | |
| 6,765,780 B2 | 7/2004 | Brendel et al. | |
| 6,882,248 B2 | 4/2005 | Stevenson | |
| 6,888,715 B2 | 5/2005 | Stevenson | |
| 6,895,276 B2 | 5/2005 | Kast | |

(Continued)

FOREIGN PATENT DOCUMENTS

| EP | 1400993 | 3/2004 |
|---|---|---|
| EP | 1760735 | 3/2007 |

OTHER PUBLICATIONS

PCT/US07/066844: International Search Report dated Dec. 6, 2007.

*Primary Examiner* — Joseph Dietrich

(57) ABSTRACT

A filtering capacitor feedthrough assembly for an implantable active medical device is disclosed. The filtering capacitor feedthrough assembly includes a capacitor having an aperture defined by an inner capacitor surface. The capacitor is electrically grounded to an electrically conductive feedthrough ferrule or housing of the implantable active medical device. A terminal pin extends into the aperture. An electrically conductive split ring sleeve is disposed within the aperture and between the terminal pin and the capacitor. The split ring sleeve includes a first end, a second end, a sleeve length therebetween. A longitudinal slit through the sleeve extends from the first end to the second end. The electrically conductive split ring sleeve mechanically securing and electrically coupling the terminal pin to the capacitor.

17 Claims, 5 Drawing Sheets

U.S. PATENT DOCUMENTS

| | | |
|---|---|---|
| 6,951,664 B2 | 10/2005 | Marshall et al. |
| 6,985,349 B2 | 1/2006 | Smyth |
| 6,987,660 B2 | 1/2006 | Stevenson |
| 6,999,818 B2 | 2/2006 | Stevenson |
| 7,012,192 B2 | 3/2006 | Stevenson |
| 7,035,076 B1 | 4/2006 | Stevenson |
| 7,035,077 B2 | 4/2006 | Brendel |
| 7,038,900 B2 | 5/2006 | Stevenson |
| 7,047,077 B2 | 5/2006 | Hansen |
| 7,136,273 B2 | 11/2006 | Stevenson |
| 7,187,535 B1 | 3/2007 | Iyer et al. |
| 7,199,995 B2 | 4/2007 | Stevenson |
| 7,310,216 B2 | 12/2007 | Stevenson |
| 7,489,495 B2 | 2/2009 | Stevenson |
| 7,502,217 B2 | 3/2009 | Zhao et al. |
| 7,535,693 B2 | 5/2009 | Stevenson |
| 7,623,335 B2 | 11/2009 | Stevenson |
| 7,765,005 B2 | 7/2010 | Stevenson |
| 2005/0060003 A1 | 3/2005 | Taylor |
| 2005/0201039 A1 | 9/2005 | Stevenson |
| 2006/0167522 A1 | 7/2006 | Malinowski |
| 2008/0208278 A1 | 8/2008 | Janzig et al. |

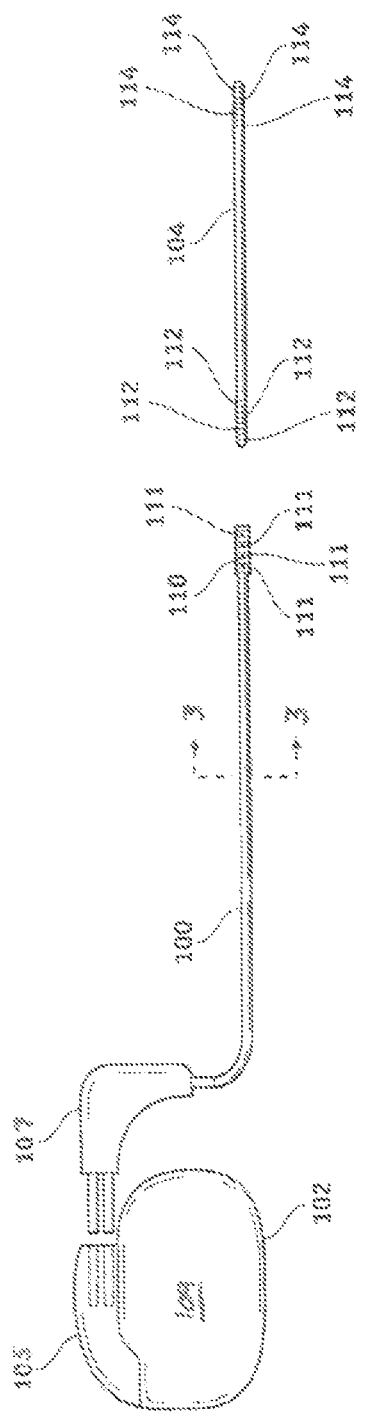
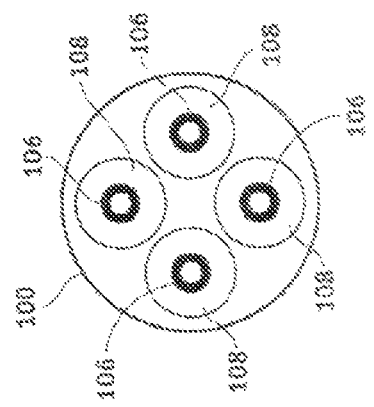

FILTERING CAPACITOR FEEDTHROUGH ASSEMBLY

The present application is a divisional of U.S. patent application Ser. No. 11/688,985, filed Mar. 21, 2007, now allowed, which application is hereby incorporated by reference as if re-written in its entirety.

FIELD

The present disclosure relates to a filtering capacitor feedthrough assembly for an implantable device.

BACKGROUND

Implantable active medical devices, such as cardiac disease rhythm management devices (pacemakers and defibrillators) and a variety of implantable muscle/nerve stimulators generally include a battery and battery-powered electronic pulse generator contained within a hermetically sealed housing or case and attached to a lead connector housing or block. The lead connector block is often affixed to the hermetically sealed housing with brackets, metal solder, and/or a medical grade adhesive.

Electronics within the hermetically sealed housing are conductively coupled to the lead connector block with an electrical feedthrough assembly. Electrical feedthroughs serve the purpose of providing a conductive path extending between the interior of a hermetically sealed container and a point outside the hermetically sealed housing. The conductive path through the feedthrough usually includes a conductor pin or terminal that is electrically insulated from the hermetically sealed housing. Feedthrough assemblies are known in the art to provide the conductive path and seal the electrical container from its ambient environment. Such feedthroughs include a ferrule, and an insulative material such as a hermetic glass or ceramic seal that positions and insulates the pin within the ferrule. Sometimes it is desired that the electrical device include a capacitor within the ferrule and around the terminal, thus shunting any electromagnetic interference (EMI) at high frequencies at the entrance to the electrical device to which the feedthrough device is attached. The capacitor electrically contacts the pin lead and the ferrule.

The pin lead/capacitor and capacitor/ferrule connection has been made using solder, weld, braze, and conductive adhesives. While this arrangement has proven to be highly reliable, it involves a variety of expensive manufacturing processes and parts that necessarily increase the cost of the resulting product.

BRIEF SUMMARY

The present disclosure relates to a filtering capacitor feedthrough assembly for an implantable device. A split ring sleeve mechanically secures and electrically couples a terminal pin to filtering capacitor and/or a tapered wedge element mechanically secures and electrically couples a filtering capacitor to a ferrule or housing.

In a first embodiment, a filtering capacitor feedthrough assembly includes a capacitor having an aperture defined by an inner capacitor surface. The capacitor is electrically grounded to an electrically conductive feedthrough ferrule or housing of the implantable active medical device. A terminal pin extends into the aperture. An electrically conductive split ring sleeve is disposed within the aperture and between the terminal pin and the capacitor. The split ring sleeve includes a first end, a second end, and a sleeve length therebetween. A longitudinal slit through the sleeve extends from the first end to the second end. The electrically conductive split ring sleeve mechanically securing and electrically coupling the terminal pin to the capacitor.

In another embodiment, an implantable active medical device includes a hermetically sealed housing, electronics disposed within the sealed housing, a lead connector attached to the hermetically sealed housing, and a filtering capacitor feedthrough assembly electrically connecting the electronics and the lead connector. The filtering capacitor feedthrough assembly includes a capacitor having an aperture defined by an inner capacitor surface. The capacitor electrically grounded to the hermetically sealed housing. A terminal pin extends into the aperture. The terminal pin electrically connects the electronics and the lead connector. An electrically conductive split ring sleeve is disposed within the aperture and between the terminal pin and the capacitor. The split ring sleeve includes a first end, a second end, a sleeve length therebetween, and a longitudinal slit through the sleeve extending from the first end to the second end. The electrically conductive split ring sleeve mechanically secures and electrically couples the terminal pin to the capacitor.

In a further embodiment, a method of forming a filtering capacitor feedthrough assembly for an implantable active medical device includes providing a capacitor having an aperture defined by an inner capacitor surface, the capacitor is electrically grounded to an electrically conductive feedthrough ferrule or housing of the implantable active medical device. The method also includes, inserting a terminal pin into the aperture, and disposing an electrically conductive split ring sleeve within the aperture and between the terminal pin and the capacitor. The split ring sleeve includes a first end, a second end, a sleeve length therebetween, and a longitudinal slit through the sleeve extending from the first end to the second end. The electrically conductive split ring sleeve mechanically secures and electrically couples the terminal pin to the capacitor.

In another embodiment, a filtering capacitor feedthrough assembly for an implantable active medical device includes a capacitor having an aperture, the capacitor being mechanically secured and electrically grounded to an electrically conductive feedthrough ferrule or housing of the implantable active medical device with an electrically conductive tapered wedge element. A terminal pin is electrically isolated from the conductive feedthrough ferrule or housing of the implantable active medical device. The terminal pin extends into the aperture and the terminal pin is mechanically secured and electrically coupled to the capacitor.

BRIEF DESCRIPTION OF THE DRAWINGS

The invention may be more completely understood in consideration of the following detailed description of various embodiments of the invention in connection with the accompanying drawings, in which:

FIG. 2 is a schematic exploded view of an implantable active medical device;

FIG. 3 is a schematic cross-sectional view of an lead body shown in FIG. 2 taken along line 3-3;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
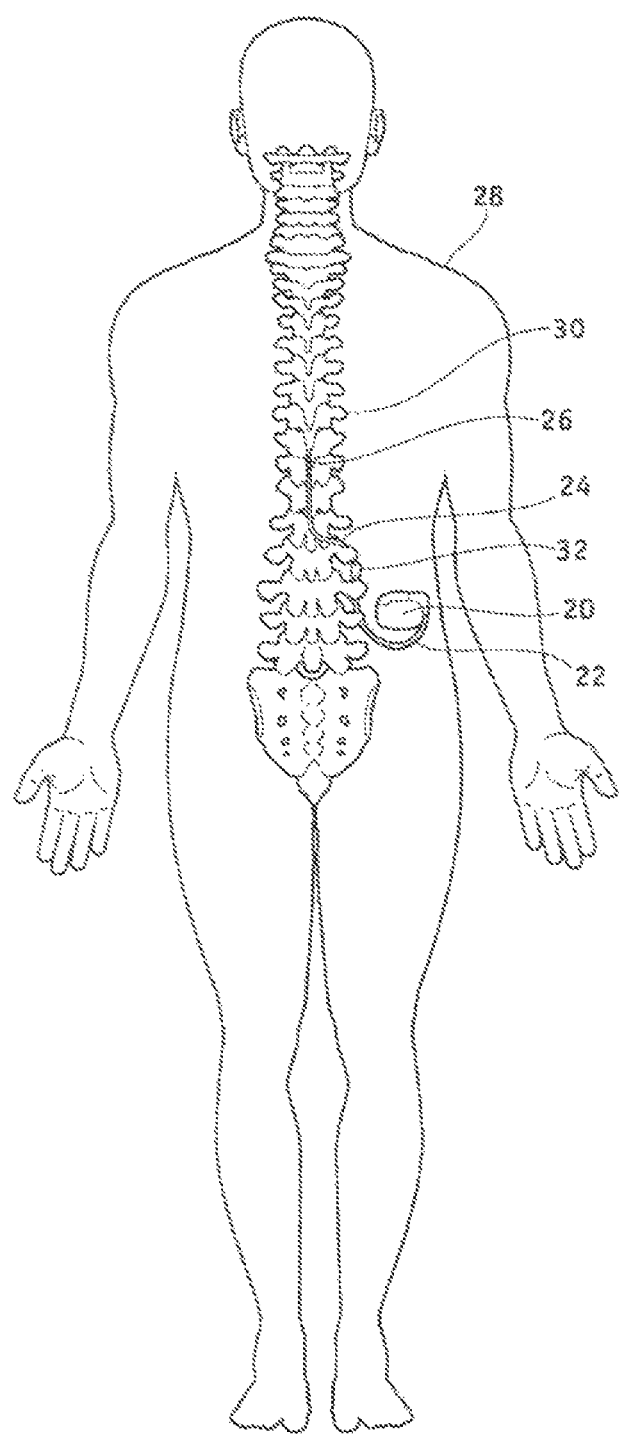
FIG. 1 is a schematic diagram of a an active medical device implanted within a human body.

In the following description, reference is made to the accompanying drawings that form a part hereof, and in which are shown by way of illustration several specific embodiments. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "active implantable medical device" includes, for example, a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, or a gastric pacemaker, and the like.

The term "hermetic seal", "hermetically sealed" are used interchangeably and refer to an airtight seal. This term is often used to describe electronic parts that are designed and intended to secure against the entry of microorganisms, water, oxygen, and the like, and to maintain the safety and quality of their contents.

The present disclosure relates to a filtering capacitor feedthrough assembly for an implantable device. In particular, this disclosure is directed to the use of a split ring sleeve to mechanically connect a feedthrough pin or terminal to a filtering capacitor and enable an electrical pathway between the capacitor and the feedthrough pin or terminal. This disclosure is also directed to the use of a tapered wedge element to mechanically connect a filtering capacitor to a ferrule or device housing and enable an electrical ground pathway between the capacitor and the ferrule or device housing. While the present invention is not so limited, an appreciation of various aspects of the invention will be gained through a discussion of the examples provided below.

FIG. 1 is a schematic diagram of an active medical device 20 implanted within a human body or patient 28. The implanted active medical device 20 is illustrated as a neurostimulator, however, the implanted active medical device 20 can be any "active implantable medical device" as described above and can be placed in any location within a body cavity and capable of stimulating any organ or tissue within the body, as desired.

The active medical device 20 includes a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30. The active medical device 20 can have one or two leads each having four to eight electrodes, as desired. Such a system may also include a physician programmer and a patient programmer (not shown). The active medical device 20 can be considered to be an implantable pulse generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of pulses or signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad™ lead available from Medtronic, Inc.), and some are designed to be surgically implanted (e.g. Model 3998 Specify™ lead, also available from Medtronic, Inc.). In some embodiments, the lead 24 may contain a paddle at its distant end for housing electrodes 26. In many embodiments, electrodes 26 may include one or more ring contacts at the distal end of lead 24.

FIG. 2 is a schematic exploded view of the implantable active medical device described above and FIG. 3 is a schematic cross-sectional view of the lead extension body 100 shown in FIG. 2 taken along line 3-3. The implantable active medical device includes a lead extension 100 configured to be coupled between an implantable active medical device 102 and the lead 104. The proximal portion of lead extension 100 includes a lead connector plug 107 configured to be received or plugged into lead connector 105 of the implantable active medical device 102 through a hermetically sealed housing 109 of the implantable active medical device 102. The distal end of lead extension 100 includes a connector 110 including internal contacts 111, and is configured to receive the proximal end of lead 104 having contacts 112 thereon. The distal end of lead 104 includes distal electrodes 114 that are in electrical connection with corresponding contacts 112.

In many embodiments, the lead extension 100 has a diameter of approximately 0.1 inch, which can be larger than that of lead 104 so as to make extension 100 more durable than lead 104. In many embodiments, lead extension 100 can differ from lead 104 in that each filer 106 in the lead body is helically wound or coiled in its own lumen 108 and not co-radially wound with the rest of the filers as can be the case in lead 104. In many embodiments, the diameter of the lead is approximately 0.05 inch. This diameter can be based upon the diameter of the needle utilized in the surgical procedure to deploy the lead and upon other clinical anatomical requirements. In many embodiments, the length of such lead can be based upon other clinical anatomical requirements and can be 28 centimeters; however, other lengths are utilized to meet particular needs of specific patients and to accommodate special implant locations.

The active medical device 102 includes a hermetically sealed housing 109 defining a sealed housing interior. A battery and electronics are in electrical communication and are disposed within the hermetically sealed housing 109 interior. The electronics within the hermetically sealed housing 109 are conductively coupled to the lead connector 105 with an electrical feedthrough assembly (described below). Electrical feedthroughs serve the purpose of providing a conductive path extending between the interior of a hermetically sealed housing 109 and the lead connector 105 attached to the hermetically sealed housing 109. The conductive path through the feedthrough assembly includes a conductor pin or terminal pin that is electrically insulated from the hermetically sealed housing 109. The feedthrough includes an electrically conductive feedthrough ferrule, and an insulative material such as a hermetic glass or ceramic seal that positions and insulates the pin within the electrically conductive feedthrough ferrule. Filtered feedthroughs include a capacitor within the ferrule and around the terminal to shunt any electromagnetic interference (EMI) at high frequencies at the entrance to the electrical device to which the feedthrough assembly is attached. The capacitor electrically contacts the pin lead and the ferrule. The terminal pin electrically connects the electronics within the sealed housing to the lead connector.

Figure 4:
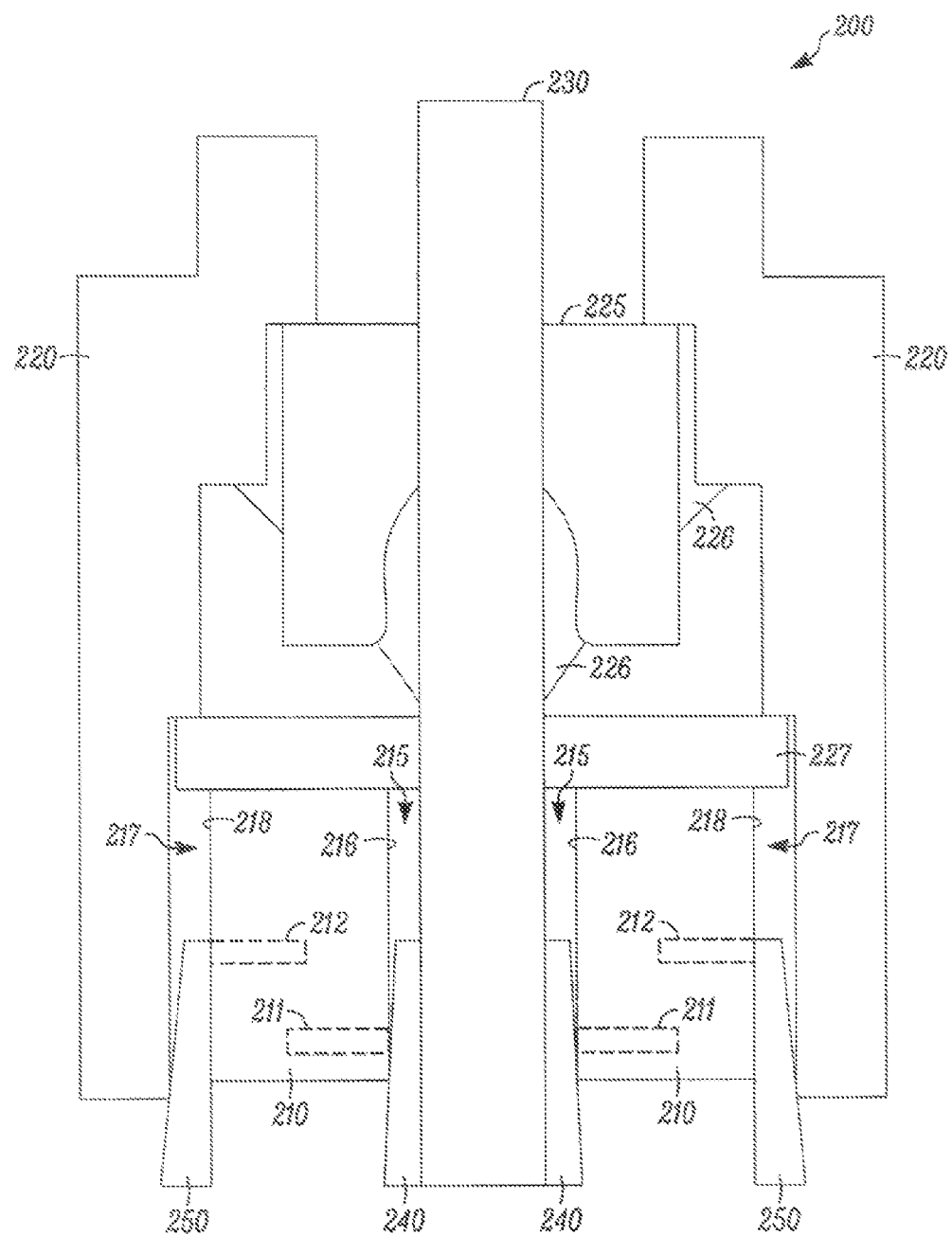
FIG. 4 is a schematic cross-sectional view of an illustrative filtering capacitor feedthrough assembly.

FIG. 4 is a schematic cross-sectional diagram of an illustrative filtering capacitor feedthrough assembly 200. The filtering capacitor feedthrough assembly 200 includes a capacitor 210 having an aperture 215 defined by an inner surface 216 of the capacitor 210. In many embodiments, the aperture 215 extends all the way through the capacitor 210 forming a cylindrical lumen through the capacitor 210. The inner surface 216 of the capacitor 210 is in electrical contact with active plates 211 within the capacitor 210. An outer surface 218 of the capacitor 210 is in electrical contact with ground plates 212 within the capacitor 210. A single active plate 211 and a single ground plate 212 is illustrated, however it is understood that the capacitor 210 includes a plurality of active plates 211 and a plurality of ground plates 212, as is known in the art.

A terminal pin 230 extends into the aperture 215 of the capacitor 210. In many embodiments, the terminal pin 230 extends through the aperture 215 of the capacitor 210. An electrically conductive split ring sleeve 240 is disposed within the aperture 215 and between the terminal pin 230 and the capacitor 210. The electrically conductive split ring sleeve 240 mechanically secures and electrically couples the terminal pin 230 to the capacitor 210 inner surface 216. In many embodiments, the electrically conductive split ring sleeve 240 has a first end, a second end, a sleeve length disposed therebetween, and a longitudinal slit through the sleeve extends from the first end to the second end (as described in relation to FIGS. 5A-5C). The terminal pin 230 is disposed within the inner diameter of the conductive split ring sleeve 240. Thus, the conductive split ring sleeve 240 is axially disposed about the terminal pin 230. In some embodiments, the conductive split ring sleeve 240 is fixed to the terminal pin 230 and/or the inner surface 216 of the capacitor 210. The conductive split ring sleeve 240 can be fixed with any useful method or material such as, for example, solder, weld, braze or conductive adhesive.

In many embodiments, the electrically conductive split ring sleeve 240 first end has a circumference that is greater than the second end. In many embodiments, the electrically conductive split ring sleeve 240 is tapered such that the first end of the split ring sleeve has a first sleeve thickness value that is greater than the second end second sleeve thickness value. Thus, the electrically conductive split ring sleeve 240 can be axially disposed about the terminal pin 230 and slid along the terminal pin 230 into the aperture 215 until the electrically conductive split ring sleeve 240 is in frictional engagement with both the inner capacitor surface 216 and the terminal pin 230. The frictional engagement or interference fit of the electrically conductive split ring sleeve 240 between the inner capacitor surface 216 and the terminal pin 230 provides the mechanical fastening and electrical coupling of the inner capacitor surface 216 and the terminal pin 230.

The terminal pin 230 extends through the ferrule 220 or housing and is in a non-conductive relation to the ferrule 220 or housing. An insulator 225 is disposed between the terminal pin 230 and the ferrule 220 or housing. The insulator 225 is disposed fixed to the terminal pin 230 and the ferrule 220 or housing with solder, weld, braze or adhesive 226, as desired to provide a hermetic seal. An optional second insulator 227 is disposed within the ferrule 220 or housing and adjacent to the capacitor 210.

The outer surface 218 of the capacitor 210 is electrically grounded to the electrically conductive feedthrough ferrule 220 or housing of the implantable active medical device. In some embodiments, an electrically conductive tapered wedge element 250 is disposed within an aperture 217 defined by the outer surface 218 of the capacitor 210 and the electrically conductive feedthrough ferrule 220 or housing. The electrically conductive tapered wedge element 250 mechanically secures and electrically couples the capacitor 210 to the electrically conductive feedthrough ferrule 220 or housing.

In many embodiments, the electrically conductive tapered wedge element 250 is tapered such that a first end of the tapered wedge element 250 has a first wedge thickness value that is greater than a second end second wedge thickness value. Thus, the tapered wedge element 250 is axially disposed about the capacitor 210. The conductive tapered wedge element 250 can be axially disposed about the capacitor 210 and forced into the aperture 217 until the electrically conductive tapered wedge element 250 is in frictional engagement with both the capacitor outer surface 218 and the electrically conductive feedthrough ferrule 220 or housing. The frictional engagement or interference fit of the electrically conductive tapered wedge element 250 between the capacitor outer surface 218 and the electrically conductive feedthrough ferrule 220 or housing provides the mechanical fastening and electrical coupling of the capacitor outer surface 218 and the electrically conductive feedthrough ferrule 220 or housing.

Figure 5A:
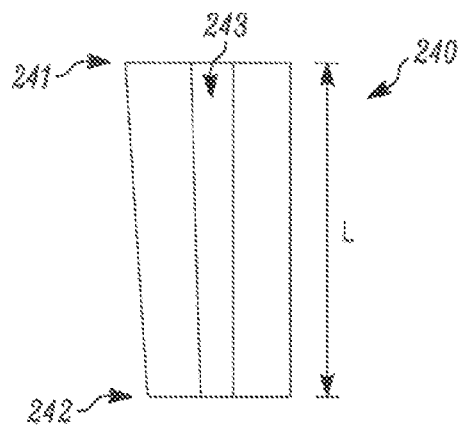
FIG. 5A is a side elevation view of an illustrative split ring sleeve utilized in a filtering capacitor feedthrough assembly.
Figure 5B:
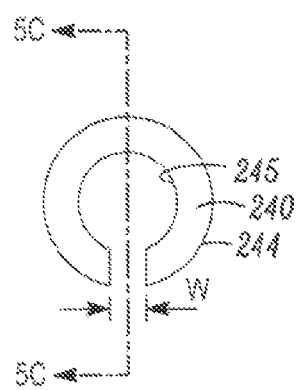
FIG. 5B is a top view of the illustrative split ring sleeve shown in FIG. 5A.
Figure 5C:
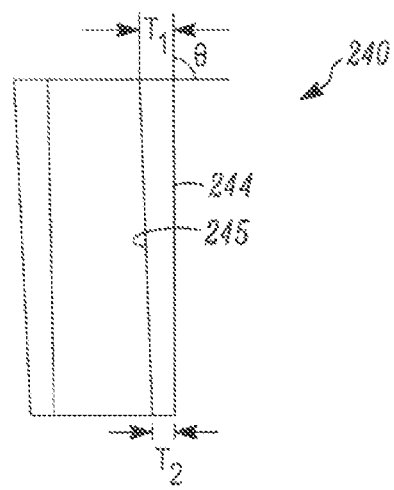
FIG. 5C is a side elevation cross-sectional view of the split ring sleeve shown in FIG. 5B.

FIG. 5A is a side elevation view of an illustrative split ring sleeve 240 utilized in a filtering capacitor feedthrough assembly described herein. FIG. 5B is a top view of the illustrative split ring sleeve 240 shown in FIG. 5A. FIG. 5C is a side elevation cross-sectional view of the split ring sleeve 240 shown in FIGS. 5A and 5B. The illustrated electrically conductive split ring sleeve 240 has a first end 241, a second end 242, a sleeve length L disposed therebetween, and a longitudinal slit 243 through the sleeve 240 extends from the first end 241 to the second end 242. The longitudinal slit 243 has a width W. In many embodiments, the longitudinal slit 243 a width W reduces as the split ring sleeve 240 is forced into the aperture 215 (see FIG. 4).

The split ring sleeve 240 is defined by an outer surface 244 and an opposing inner surface 245. In many embodiments, the split ring sleeve first end 241 has a circumference that is greater than the second end 242. In many embodiments, the first end 241 has a first sleeve thickness value $T_1$ that is greater than the second end 242 second sleeve thickness value $T_2$. The taper of the split ring sleeve 240 can be defined by an angle φ defined by the angle between a longitudinal axis and the outer surface 244 plane, as illustrated. In many embodiments, the angle φ is less than 90 degrees, or from 85 to 89 degrees, or from 87 to 89 degrees.

The split ring sleeve 240 can be formed of any useful solid mechanically stable and electrically conductive material. The solid mechanically stable and electrically conductive material is able to withstand enough pressure to force the split ring sleeve 240 into the aperture 215 (see FIG. 4) without failure and is able to mechanically secure the inner capacitor surface 216 and the terminal pin 230 (see FIG. 4) via frictional engagement. A partial listing of useful metallic materials includes copper, nickel, aluminum, steel, tantalum, niobium, titanium, platinum, iridium, silver, molybdenum, zirconium, vanadium, tungsten, rhodium, rhenium, oxmium, ruthenium, palladium, silver, and alloys, mixtures or combinations thereof. The split ring sleeve 240 can include two or more metallic layers. In many of these embodiments, a core layer can includes the metallic materials described above and an outer noble metal (e.g., platinum, gold, silver) layer is disposed on the core layer. In many embodiments, the split ring sleeve 240 is be formed of a solid, mechanically stable and electrically conductive metallic material having a glass transition temperature value being greater than 175 degrees centigrade, or greater than 200 degrees centigrade, or greater than 250 degrees centigrade, or greater than 300 degrees centigrade.

The split ring sleeve 240 can be formed with any useful method. In some embodiments, the split ring sleeve 240 is formed by wrapping a sheet of metallic material about a mandrel to form a hollow tapered cylinder and then removing the mandrel from the hollow tapered cylinder material to provide the split ring sleeve 240.

The split ring sleeve 240 can have any useful dimensions, depending on the application. In some embodiments, the split ring sleeve 240 has a length in a range from 500 to 5000 micrometers, a sleeve thickness in a range from 50 to 250 micrometers, and a diameter in a range from 200 to 600 micrometers. In many embodiments, the longitudinal slit 243 has a width W in a range such that the width W reduces to less than 25 micrometers when the split ring sleeve 240 is forced into the aperture 215 (see FIG. 4). In some embodiments the longitudinal slit 243 has a width W in a range such that the width W completely closes when the split ring sleeve 240 is forced into the aperture 215 (see FIG. 4).

The tapered wedge element 250 can be formed of the conductive materials described above and can also include two or more metallic layers. In many of these embodiments, a core layer can includes the metallic materials described above and an outer noble metal (e.g., platinum, gold, silver) layer is disposed on the core layer. The tapered wedge element 250 can be formed of any useful solid mechanically stable and electrically conductive material. The solid mechanically stable and electrically conductive material is able to withstand enough pressure to force the tapered wedge element 250 into the aperture 217 (see FIG. 4) without failure and is able to mechanically secure the outer capacitor surface 218 and the electrically conductive feedthrough ferrule 220 or housing (see FIG. 4) via frictional engagement.

Figure 6:
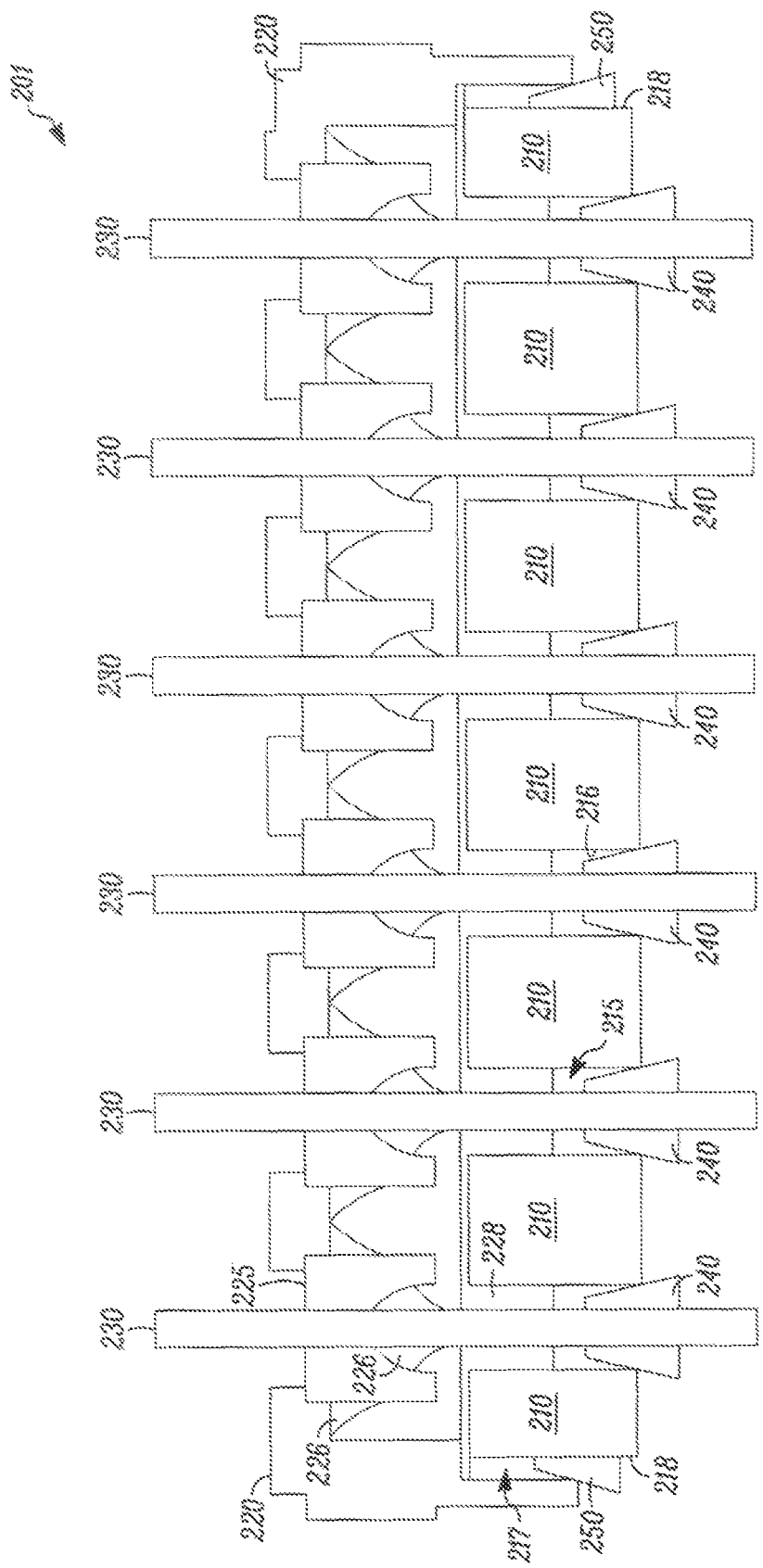
FIG. 6 is a schematic cross-sectional diagram of another illustrative filtering capacitor feedthrough assembly.

FIG. 6 is a schematic cross-sectional diagram of another illustrative filtering capacitor feedthrough assembly 201. In this embodiment, six terminal pins 230 are disposed through the feedthrough assembly 201. The first terminal pin 230 is now described, the five remaining pins 230 have a substantially similar description and is not repeated but understood to be the same.

The filtering capacitor feedthrough assembly 201 includes a capacitor 210 having a plurality of apertures 215 defined by an inner surface 216 of the capacitor 210. In many embodiments, the apertures 215 extend all the way through the capacitor 210 forming a plurality of cylindrical lumens through the capacitor 210. The inner surface 216 of the capacitor 210 is in electrical contact with active plates within the capacitor 210. An outer surface 218 of the capacitor 210 is in electrical contact with ground plates within the capacitor 210.

A terminal pin 230 extends into each corresponding aperture 215 of the capacitor 210. In many embodiments, the terminal pin 230 extends through the aperture 215 of the capacitor 210. A split ring sleeve 240 is disposed within the aperture 215 and between the terminal pin 230 and the capacitor 210. The electrically conductive split ring sleeve 240 mechanically secures and electrically couples the each terminal pin 230 to the respective capacitor 210 inner surface 216. As described above, the terminal pin 230 is disposed within the inner diameter of the conductive split ring sleeve 240. Thus, the split ring sleeve 240 is axially disposed about the terminal pin 230. In some embodiments, the conductive split ring sleeve 240 is fixed to the corresponding terminal pin 230 and/or inner surface 216 of the capacitor 210. The conductive split ring sleeve 240 can be fixed with any useful method or material such as, for example, solder, weld, braze or conductive adhesive.

In many embodiments, the electrically conductive split ring sleeve 240 first end has a circumference that is greater than the second end. In many embodiments, the electrically conductive split ring sleeve 240 is tapered such that the first end of the split ring sleeve has a first sleeve thickness value that is greater than the second end second sleeve thickness value. Thus, the electrically conductive split ring sleeve 240 can be axially disposed about the terminal pin 230 and slid along the terminal pin 230 into the aperture 215 until the electrically conductive split ring sleeve 240 is in frictional engagement with both the inner capacitor surface 216 and the terminal pin 230. The frictional engagement or interference fit of the electrically conductive split ring sleeve 240 between the inner capacitor surface 216 and the terminal pin 230 provides the mechanical fastening and electrical coupling of the inner capacitor surface 216 and the terminal pin 230.

The terminal pin 230 extends through the ferrule 220 and housing and is in a non-conductive relation to the ferrule 220 and housing. An insulator 225 is disposed between the terminal pin 230 and the ferrule 220. The insulator 225 is fixed to the terminal pin 230 and the ferrule 220 with solder, weld, braze or adhesive 226, as desired to provide a hermetic seal.

The outer surface 218 of the capacitor 210 is electrically grounded to an electrically conductive feedthrough ferrule 220 of the implantable active medical device. In some embodiments, an electrically conductive tapered wedge element 250 is disposed between the outer surface 218 of the capacitor 210 and the electrically conductive feedthrough ferrule 220, as described above. The electrically conductive tapered wedge element 250 mechanically secures and electrically couples the capacitor 210 to the electrically conductive feedthrough ferrule 220.

In many embodiments, the electrically conductive tapered wedge element 250 is tapered such that a first end of the tapered wedge element 250 has a first wedge thickness value that is greater than a second end second wedge thickness value. Thus, the tapered wedge element 250 is axially disposed about the capacitor 210. The conductive tapered wedge element 250 can be axially disposed about the capacitor 210 and forced into the aperture 217 until the electrically conductive tapered wedge element 250 is in frictional engagement with both the capacitor outer surface 218 and the electrically conductive feedthrough ferrule 220 or housing. The frictional engagement or interference fit of the electrically conductive tapered wedge element 250 between the capacitor outer surface 218 and the electrically conductive feedthrough ferrule 220 or housing provides the mechanical fastening and electrical coupling of the capacitor outer surface 218 and the electrically conductive feedthrough ferrule 220 or housing.

In some embodiments, solder, weld, braze or conductive adhesive 228 can be placed adjacent to split ring sleeve 240 and/or tapered wedge element 250 to assist in mechanically securing and electrically coupling adjacent surfaces, as desired.

Thus, embodiments of the FILTERING CAPACITOR FEEDTHROUGH ASSEMBLY are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A filtering capacitor feedthrough assembly for an implantable active medical device comprising:
   a capacitor having an aperture, the capacitor being mechanically secured and electrically grounded to an electrically conductive feedthrough ferrule or housing of the implantable active medical device;
   a terminal pin electrically isolated from the conductive feedthrough ferrule or housing of the implantable active medical device, the terminal pin extending into the aperture, the terminal pin mechanically secured and electrically coupled to the capacitor with an electrically conductive tapered wedge element.

2. The filtering capacitor feedthrough assembly according to claim 1, wherein the electrically conductive tapered wedge element mechanically secures and electrically couples the terminal pin to an inner capacitor surface defining the aperture of the capacitor.

3. The filtering capacitor feedthrough assembly according to claim 1, wherein the electrically conductive tapered wedge element includes a first end, a second end, a sleeve length therebetween, and a longitudinal slit through the sleeve extends from the first end to the second end.

4. The filtering capacitor feedthrough assembly according to claim 3, wherein the electrically conductive tapered wedge element end has a circumference that is greater than the second end.

5. The filtering capacitor feedthrough assembly according to claim 3, wherein the first end has a first sleeve thickness value that is greater than the second end second sleeve thickness value.

6. The filtering capacitor feedthrough assembly according to claim 1, wherein the electrically conductive tapered wedge element is fixed to the terminal pin.

7. The filtering capacitor feedthrough assembly according to claim 1, wherein the electrically conductive tapered wedge element comprises two or more metallic layers.

8. The filtering capacitor feedthrough assembly according to claim 2, wherein the electrically conductive tapered wedge element is defined by an outer sleeve surface, an opposing inner sleeve surface, and a sleeve thickness therebetween, and a majority the outer sleeve surface is in contact with the inner capacitor surface and a majority of the inner sleeve surface is in contact with the terminal pin.

9. The filtering capacitor feedthrough assembly according to claim 2, wherein the electrically conductive tapered wedge element is a tapered hollow cylinder.

10. The filtering capacitor feedthrough assembly according to claim 2, wherein the electrically conductive tapered wedge element mechanically secures and electrically couples the terminal pin to the capacitor by frictional engagement or interference fit of the electrically conductive tapered wedge element between the inner capacitor surface and the terminal pin.

11. An implantable active medical device comprising:
    a hermetically sealed housing;
    electronics disposed within the sealed housing;
    a lead connector attached to the hermetically sealed housing; and
    a filtering capacitor feedthrough assembly electrically connecting the electronics and the lead connector, the filtering capacitor feedthrough assembly comprising:
      a capacitor having an aperture defined by an inner capacitor surface, the capacitor electrically grounded to the hermetically sealed housing;
      a terminal pin extending into the aperture, the terminal pin electrically connecting the electronics and the lead connector; and
      an electrically conductive split ring sleeve disposed within the aperture and between the terminal pin and the capacitor, the split ring sleeve includes a first end, a second end, a sleeve length therebetween, and a longitudinal slit through the sleeve extending from the first end to the second end, the electrically conductive split ring sleeve mechanically securing and electrically coupling the terminal pin to the capacitor by frictional engagement or interference fit of the electrically conductive split ring sleeve between the inner capacitor surface and the terminal pin.

12. The implantable active medical device according to claim 11, wherein the split ring sleeve is a tapered hollow cylinder.

13. The implantable active medical device according to claim 11, wherein the split ring sleeve is defined by an outer sleeve surface, an opposing inner sleeve surface, and a sleeve thickness therebetween, and a majority the outer sleeve surface is in contact with the inner capacitor surface and a majority of the inner sleeve surface is in contact with the terminal pin.

14. The implantable active medical device according to claim 11, wherein the split ring sleeve first end has a circumference that is greater than the second end.

15. The implantable active medical device according to claim 11, wherein the first end has a first sleeve thickness value that is greater than the second end second sleeve thickness value.

16. The implantable active medical device according to claim 11, wherein the split ring sleeve is fixed to the terminal pin.

17. The implantable active medical device according to claim 11, wherein the split ring sleeve comprises two or more metallic layers.

\* \* \* \* \*